United States Patent
Kim et al.

(10) Patent No.: US 9,562,093 B2
(45) Date of Patent: Feb. 7, 2017

(54) ANTIBODIES OR ANTIGEN-BINDING FRAGMENTS THEREOF SPECIFICALLY BINDING TO VEGF-C AND USE THEREOF

(71) Applicant: Samsung Electronics Co., Ltd., Suwon-si, Gyeonggi-do (KR)

(72) Inventors: Seok Kyun Kim, Seoul (KR); Sang Yeul Han, Yongin-si (KR); Kwang Hoon Lee, Osan-si (KR); Kyung Eun Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 43 days.

(21) Appl. No.: 14/518,502

(22) Filed: Oct. 20, 2014

(65) Prior Publication Data

US 2015/0110787 A1    Apr. 23, 2015

(30) Foreign Application Priority Data

Oct. 18, 2013  (KR) .................. 10-2013-0124812

(51) Int. Cl.
*A61K 39/395* (2006.01)
*C07K 16/18* (2006.01)
*C07K 16/22* (2006.01)

(52) U.S. Cl.
CPC ........... *C07K 16/22* (2013.01); *C07K 2317/21* (2013.01); *C07K 2317/622* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 7,423,125 B2 | 9/2008 | Alitalo et al. |
| 2004/0147726 A1 | 7/2004 | Alitalo et al. |
| 2006/0025331 A1 | 2/2006 | Hu et al. |
| 2009/0017011 A1 | 1/2009 | Alitalo et al. |
| 2009/0169551 A1 | 7/2009 | McColl et al. |
| 2012/0052566 A9 | 3/2012 | Bagri et al. |
| 2012/0207671 A1 | 8/2012 | Baldwin |
| 2012/0230992 A1 | 9/2012 | Lee et al. |

FOREIGN PATENT DOCUMENTS

EP    1119371 B1    10/1998

OTHER PUBLICATIONS

Vajdos et al. (J. Mol. Biol. Jul. 5, 2002, 320(2):415-428).*
(Paul, Fundamental Immunology, 3rd Edition, 1993, pp. 292-295).*
He et al., "Suppression of Tumor Lymphangiogenesis and Lymph Node Metastasis by Blocking Vascular Endothelial Growth Factor Receptor 3 Signaling", *Journal of the National Cancer Institute*, 94(11): 819-825 (2002).
Karkkainen et al., "Lymphatic endothelial regulation, lymphoedema, and lymph node metastasis", *Seminars in Cell & Developmental Biology*, 13:9-18 (2002).
Stacker et al., "The role of tumor lymphangiogenesis in metastatic spread", *FASEB Journal*, 16:922-934 (2002).

* cited by examiner

*Primary Examiner* — Christine J Saoud
(74) *Attorney, Agent, or Firm* — Leydig, Voit & Mayer, Ltd.

(57) ABSTRACT

An antibody or antigen-binding fragment thereof that specifically binds to and inhibits VEGF-C and uses thereof in a method of inhibiting angiogenesis and a method of preventing, treating, and/or diagnosing a disease associated with activation and/or overexpression of VEGF-C, using the antibody, and a method of detecting the presence of VEGF-C in a sample.

11 Claims, 3 Drawing Sheets

ANTIBODIES OR ANTIGEN-BINDING FRAGMENTS THEREOF SPECIFICALLY BINDING TO VEGF-C AND USE THEREOF

CROSS-REFERENCE TO RELATED APPLICATIONS

This application claims the benefit of Korean Patent Application No. 10-2013-0124812 filed on Oct. 18, 2013 in the Korean Intellectual Property Office, the entire disclosures of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: 7,015 bytes ASCII (Text) file named "718578 ST25-Revised.TXT|" created Jun. 22, 2016.

BACKGROUND

1. Field

Provided is a polypeptide which specifically binds to and inhibits VEGF-C (Vascular endothelial growth factor-C), and a uses thereof. In particular, provided are a polypeptide that binds to VEGF-C (e.g., a VEGF-C antagonist), an anti-VEGF-C antibody, a method of inhibiting angiogenesis and a method of preventing, treating, and/or diagnosing a disease associated with activation and/or overexpression of VEGF-C, using the peptide or antibody.

2. Description of the Related Art

Angiogenesis refers to a physiological process through which new blood vessels form from pre-existing vessels, and plays an important role in formation of organs, normal physiological growth, wound healing, and the like. In addition, abnormal angiogenesis is critically involved in a disease such as tumor growth, development, or metastasis, age-related macular degeneration, diabetic retinopathy, psoriasis, rheumatic arthritis, chronic inflammation, and the like.

In particular, angiogenesis plays an important role in tumor growth or metastasis. For these reasons, various in-depth studies on the biological mechanisms involved in angiogenesis have been conducted by many global pharmaceutical companies. Most of the studies are based on the concept that inhibition or limitation of blood supply to tumor cells may lead to decreasing oxygen and nutrient supply to the tumor cells, thereby inhibiting the growth and proliferation of the tumor cells. One of targets of the studies is vascular endothelial growth factor (VEGF) family of which VEGF-A, VEGF-B, VEGF-C, VEGF-D have been identified.

Tumor metastasis to local lymph node through lymphatic vessel is a general step in cancer progress. The metastasis is an important prognostic factor in various cancers, and provides a standard for surgical and radiation therapy of local lymph node. The tumor metastasis occurs via local infiltration and destruction of intercellular matrix, intravasation into blood vessel, transport through lymph or other channel, survival in circulating blood, extravasation from blood vessel at secondary region, and proliferation at new location, in order (see Idler, et al., Adv. Cancer Res. 28, 149-250 (1978), Liotta, et al., Cancer Treatment Res. 40, 223-238 (1988), Nicolson, Biochim. Biophy. Acta 948, 175-224 (1988) and Zetter, N. Eng. J. Med. 322, 605-612 (1990)).

Recently, it has been reported that lymphangiogenesis and formation of lymphatic vessel promote the lymph node metastasis, and thus, the inhibition of lymphangiogenesis can provide a new strategy for preventing the lymph node metastasis in cancer therapy (Stacker et al., Nature Med. 7(2), 186-191 (2001); Skobe et al., Nature Med. 7(2), 192-8 (2001); Makinen et al., Nature Med. 7(2), 199-205 (2001)).

According to recent studies, the binding of VEGF-C, which is a member of VEGF family, and its receptor, VEGFR2 or VEGFR3, promotes lymphangiogenesis, and growth and migration of lymphatic endothelial cells (see Karkkainen M J, et al., Semin Cell Dev Biol. 13:9-18 (2002)). In addition, VEGF-C promotes breast cancer metastasis, human melanoma metastasis, and lymphatic-mediated metastasis by inducing tumor-related lymphangiogenesis in various solid cancers such as a gastric cancer, human colorectal cancer, infiltrative cervical cancer, and the like. In addition, overexpression of VEGF-C in cancer cells increases the tumor-related lymphangiogenesis, thereby promoting the metastasis to local lymph nodes (see Stacker S A., et al., FASEB J 16:922-34 (2002)). Furthermore, inhibition of VEGF-C/D mediated signaling in mice leads to inhibition of lymphangiogenesis and metastasis to lymph nodes (see He Y., et al., J Natl Cancer Inst. 94:819-25 (2002)).

Although VEGF-C has recently emerged as an important target in developing anti-angiogenesis drugs, there remains a need to develop more effective and potent VEGF-C targeting drugs.

SUMMARY

Provided herein is a polypeptide comprising at least one of SEQ ID NO: 1, SEQ ID NO: 2, SEQ ID NO: 3, SEQ ID NO: 4, SEQ ID NO: 5, or SEQ ID NO: 6. In some embodiments, the polypeptide specifically binds to VEGF-C. The polypeptide also is capable of functioning as a complementarity determining region (CDR) of anti-VEGF-C antibody.

Also provided is an antagonist comprising a polypeptide comprising at least one of SEQ ID NO: 1, SEQ ID NO: 2, SEQ ID NO: 3, SEQ ID NO: 4, SEQ ID NO: 5, or SEQ ID NO: 6; or a polypeptide comprising SEQ ID NO: 7, a polypeptide comprising SEQ ID NO: 8, or both.

Further provided is an anti-VEGF-C antibody or an antigen-binding fragment thereof. The anti-VEGF-C antibody or an antigen-binding fragment thereof comprises at least one heavy chain complementarity determining region selected from the group consisting of a CDR-H1 comprising SEQ ID NO: 1, a CDR-H2 comprising SEQ ID NO: 2, and a CDR-H3 comprising SEQ ID NO: 3, or a heavy chain variable region including the at least one heavy chain complementarity determining region. The antibody or antibody fragment also can comprise at least one light chain complementarity determining region selected from the group consisting of CDR-L1 comprising SEQ ID NO: 4, CDR-L2 comprising SEQ ID NO: 5, and CDR-L3 comprising SEQ ID NO: 6, or a light chain variable region including the at least one light chain complementarity determining region.

Another embodiment provides a pharmaceutical composition including the anti-VEGF-C antibody or an antigen-binding fragment thereof, and/or the antagonist against VEGF-C.

Another embodiment provides a method of preventing and/or treating a disease associated with activation and/or overexpression of VEGF-C, including administering the anti-VEGF-C antibody or an antigen-binding fragment thereof, and/or the antagonist against VEGF-C, to a subject in need thereof.

Still another embodiment provides a method of detecting VEGF-C and a method of diagnosing a disease associated with the activation or overexpression of VEGF-C, using the anti-VEGF-C antibody or the antigen-binding fragment thereof, and/or the antagonist against VEGF-C. The methods involve applying the VEGF-C antagonist to a biological sample; and measuring an antigen-antagonist binding in the biological sample; wherein antigen-antagonist binding at a higher level in the biological sample than in a normal sample indicates the presence of a disease associated with activation and overexpression of VEGF-C.

Related methods and compositions also are provided, as will be apparent from the following drawings and detailed description.

DETAILED DESCRIPTION

Figure 1:
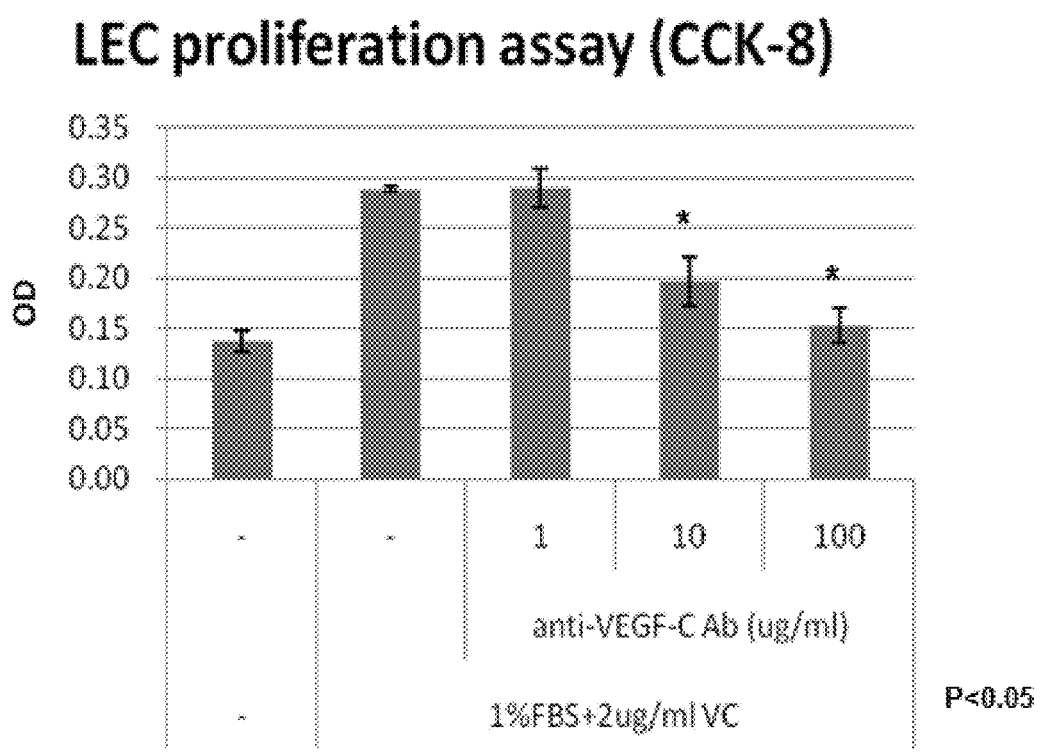
FIG. 1 is a graph displaying the proliferation level of lymphatic endothelial cells (LECs) when treated with an anti-VEGF-C antibody according to one embodiment.

The present invention concerns a polypeptide that binds to and inhibits VEGF-C and the uses thereof. In particular, provided is an antibody useful in diagnosis and treatment of a disease associated with activation and/or overexpression of VEGF-C, wherein the antibody inhibits angiogenesis in tumor tissues and inhibits cancer metastasis, by preventing VEGF-C, which is an angiogenesis inducing factor essential for cancer cell growth, from binding to its receptor, VEGF-R2 or VEGF-R3.

An embodiment provides a polypeptide including a novel amino acid sequence. In particular, the polypeptide may include or consist essentially of at least one amino acid sequence selected from the group consisting of the amino acid sequences of SEQ ID NO: 1, SEQ ID NO: 2, SEQ ID NO: 3, SEQ ID NO: 4, SEQ ID NO: 5, and SEQ ID NO: 6. The polypeptide may be characterized by its ability to specifically bind to VEGF-C, and inhibiting the functions of VEGF-C, thereby functioning as a complementarity determining region of an anti-VEGF-C antibody. Such functions of the polypeptide as a complementarity determining region of an anti-VEGF-C antibody are summarized in Table 1:

TABLE 1

| | heavy chain CDR | | light chain CDR |
|---|---|---|---|
| CDR-H1 | SYDMS (SEQ ID NO: 1) | CDR-L1 | SGSSSNIGSNNVS (SEQ ID NO: 4) |
| CDR-H2 | AISYDNGSTYYADSVKG (SEQ ID NO: 2) | CDR-L2 | YNSHRPS (SEQ ID NO: 5) |
| CDR-H3 | ARDPYLARLNTFDY (SEQ ID NO: 3) | CDR-L3 | ATWDSSLNG (SEQ ID NO: 6) |

In one embodiment, the polypeptide may include or consist essentially of the amino acid sequence of SEQ ID NO: 7, the amino acid sequence of SEQ ID NO: 8, or a combination thereof. The polypeptide including the amino acid sequence of SEQ ID NO: 7 includes or consists essentially of the amino acid sequences of SEQ ID NOS: 1 to 3, and may act as a heavy chain variable region of an anti-VEGF-C antibody. The polypeptide including the amino acid sequence of SEQ ID NO: 8 includes or consists essentially of the amino acid sequences of SEQ ID NOS: 4 to 6, and may act as a light chain variable region of an anti-VEGF-C antibody.

SEQ ID NO: 7:
EVQLLESGGGLVQPGGSLRLSCAASGFTFSSYDMSWVRQAPGKGLEWVS

AISYDNGSTYYADSVKGRFTISRDNSKNTLYLQMNSLRAEDTAVYYCAR

DPYLARLNTFDYWGQGTLVTVSS (In SEQ ID NO: 7 above, the underlined bold letters are CDR-H1, CDR-H2, and CDR-H3 in sequence)

SEQ ID NO: 8
QSVLTQPPSASGTPGQRVTISCSGSSSNIGSNNVSWYQQLPGTAPKLLI

YYNSHRPSGVPDRFSGSKSGTSASLAISGLRSEDEADYYCATWDSSLNG

YVFGGGTKLT (In SEQ ID NO: 8 above, the underlined bold letters are CDR-L1, CDR-L2, and CDR-L3 in sequence)

The polypeptide may be non-naturally occurring. The polypeptide may be recombinant or synthetic.

As mentioned above, the polypeptide specifically binds to VEGF-C (full length or partial), showing inhibitory activity against the VEGF-C. Therefore, the polypeptide may serve as a precursor or components of an antagonist against VEGF-C, for example, an anti-VEGF-C antibody, an antigen-binding fragment of the antibody, or an anti-VEGF-C antibody analogue (a structure similar in framework and function to the antibody; for example, an anti-VEGF-C peptibody, an anti-VEGF-C nanobody, etc.), or any combination thereof.

Accordingly, another embodiment provides an antagonist against VEGF-C including or consisting essentially of the polypeptide. The antagonist, which is inhibitory of VEGF-C, may be selected from the group consisting of an anti-VEGF-C antibody, an antigen-binding fragment of the antibody, an anti-VEGF-C antibody analogue (for example, a peptibody, a nanobody, a bispecific antibody, a multispecific antibody, etc.), and a combination thereof.

As used herein, the term "antagonist" is construed to encompass all molecules that partially or completely block, suppress or neutralize one or more biological activities of a target (e.g., VEGF-C). For example, an "antagonist" antibody means an antibody which suppresses or reduces the biological activity of the antigen (e.g., VEGF-C) by binding to the antigen. An antagonist binds a material which interacts with a target, to decrease the activity of the material, for example, leading to the incapacitation or death of cells which are activated by the material. Alternatively, an antagonist may discontinue interaction between the target and the material, or may substantially reduce the interaction by competing with the target for the material or by altering the tertiary structure of the material or down-regulating the material.

The term "peptibody", as used herein, means a fusion protein (peptide+antibody) mimicking an antibody in terms of framework and function in which a peptide is fused to a partial or entire constant region, e.g., Fc, of an antibody and serves as an antigen-binding fragment (heavy chain and/or light chain CDR or variable region).

The term "nanobody," also called single-domain antibody, as used herein, refers to an antibody fragment which possesses a monomeric single variable domain of an antibody and shows selectivity for certain antigens, like an intact antibody. Its molecular weights generally ranges from about 12 kDa to about 15 kDa, which is much smaller than that of an intact antibody (about 150 kDa to about 160 kDa) of an intact antibody (inclusive of two heavy chains and two light chains) and, in some cases, even than that of an Fab or scFv fragment.

The term "bispecific antibody," or "multispecific antibody," refers to an antibody which recognizes and/or binds two (bispecific) or more (multispecific) different antigens, or two or more sites of the same antigen and, as used herein, is intended to encompass a bispecific antibody or a multispecific antibody in which the polypeptide functions as one antigen-binding site.

Another embodiment provides an anti-VEGF-C antibody including the polypeptide, or an antigen-binding fragment thereof. The anti-VEGF-C antibody or an antigen-binding fragment thereof specifically recognizes or specifically binds to VEGF-C. The antigen-binding fragment may be selected from the group consisting of scFv, (scFv)$_2$, scFv-Fc, Fab, Fab' and F(ab')$_2$.

In particular, the anti-VEGF-C antibody or its antigen-binding fragment may comprise or consist essentially of:

at least one heavy chain complementarity determining region selected from the group consisting of CDR-H1 including the amino acid sequence of SEQ ID NO: 1, CDR-H2 including the amino acid sequence of SEQ ID NO: 2, and CDR-H3 including the amino acid sequence of SEQ ID NO: 3, or a heavy chain variable region including the at least one heavy chain complementarity determining region;

at least one light chain complementarity determining region selected from the group consisting of CDR-L1 including the amino acid sequence of SEQ ID NO: 4, CDR-L2 including the amino acid sequence of SEQ ID NO: 5, and CDR-L3 including the amino acid sequence of SEQ ID NO: 6, or a light chain variable region including the at least one light chain complementarity determining region;

a combination of the at least one heavy chain complementarity determining region and the at least one light chain complementarity determining region; or a combination of the at least one heavy chain variable region and the at least one light chain variable region.

For example, the anti-VEGF-C antibody or an antigen-binding fragment thereof may comprise or consist essentially of a heavy chain variable region including the amino acid sequence of SEQ ID NO: 7, a light chain variable region including the amino acid sequence of SEQ ID NO: 8, or a combination thereof.

Examples of the antibody useful in the present disclosure include, but are not limited to, animal antibodies, chimeric antibodies, humanized antibodies, and human antibodies. Also, an isolated antigen-binding fragment of an antibody may fall into the scope of the antibody of the present invention. The term "complementarity-determining region" (CDR) refers to a variable region of an antigen which is critical to specificity for an antigen. The antigen-binding fragment described above may be an antibody fragment including at least one complementarity-determining region, such as one selected from among scFv, (scFv)$_2$, scFv-Fc, Fab, Fab' and F(ab')$_2$.

The remaining portions of the anti-VEGF-C antibody or its antigen-binding fragment, that is, the parts other than the heavy chain CDR and the light chain CDR, or the heavy chain variable region and the light chain variable region, may be derived from all subtypes of immunoglobulins (e.g., IgA, IgD, IgE, IgG (IgG1, IgG2, IgG3, IgG4), IgM, etc.). By way of example, the remaining portions may be derived from light chain constant regions and/or heavy chain constant regions of all subtypes of immunoglobulins.

VEGF-C, which is a target of the anti-VEGF-C antibody or an antigen-binding fragment thereof, is a member of a vascular endothelial growth factor family, and is involved in angiogenesis, lymphangiogenesis, and/or growth of vascular endothelial cells and/or lymphatic endothelial cells. In addition, VEGF-C affects permeability of blood vessels. VEGF-C binds to and activates VEGFR-3.

The VEGF-C may be originated from a mammal such as a primate (e.g., human, monkey, etc.), a rodents such as (e.g., rat, mouse, etc.), and the like. For example, the VEGF-C may be one selected from the group consisting of a human VEGF-C (e.g., NCBI Accession No. P49767), a monkey VEGF-C (e.g., NCBI Accession No. B6EBK4), a mouse VEGF-C (e.g., NCBI Accession No. P97953), a rat VEGF-C (e.g., NCBI Accession No. O35757), and the like.

Recently, antibodies have widely been used in treatment of various diseases. Antibodies have advantages in expression and production in large quantities due to excellent stability and long half-life in vivo as well as ex vivo. In addition, antibodies have high avidity due to their numeric structures. In one embodiment, the antibody has an activity of binding to VEGF-C and preventing VEGF-C from binding to its receptor, VEGF-R2 or VEGF-R3, thereby inhibiting angiogenesis in tumor tissues. In particular, the anti-VEGF-C antibody according to an embodiment competes with VEGF-R3 in biding to VEGF-C, thereby inhibiting the binding of VEGF-C and VEGF-R3. For example, the antibody may recognize and/or bind to a VEGF-R3 binding domain of VEGF-C, thereby inhibiting the binding of VEGF-C and VEGF-R3.

Therefore, the anti-VEGF-C antibody or an antigen-binding fragment thereof may specifically recognize and/or bind to a binding region of VEGF-C, where the binding region is involved in binding to VEGF-R2 or VEGF-R3.

When a medical treatment on humans is conducted, animal-derived antibodies produced by immunizing non-immune animals with a desired antigen generally invoke immunogenicity. In the interests of suppressing such immune rejection, chimeric antibodies have been developed. Chimeric antibodies are prepared by replacing constant regions of animal-derived antibodies causing an anti-isotype response with those of human antibodies using a genetic engineering technique. Although significantly improved in anti-isotype response, compared to their original animal-derived antibodies, chimeric antibodies still retain the potential risk of side effects of anti-idiotype responses because of the animal-derived amino acids incorporated into the variable region thereof. Humanized antibodies were developed to reduce such side effects present in chimeric antibodies. Humanized antibodies are produced by grafting complementarity determining regions (CDRs), critical to antigen binding, of variable regions of chimeric antibodies to a human antibody framework.

One of the most important CDR grafting processes in producing humanized antibodies is selecting a human antibody optimized for accepting CDRs of animal-derived antibodies. To this end, advantage is taken of antibody databases, crystal structure analysis, and molecular modeling techniques. However, even when CDRs of animal-derived antibodies are grafted to an optimized human antibody framework, there may be amino acids that are positioned in the framework of the animal-derived antibody that are capable of affecting the antigen binding, which leads, in many cases, to reducing the antigen binding capabilities of the antibody. Hence, the production of humanized antibodies needs an additional antibody engineering technology for recovering the antigen binding capabilities of antibodies produced via humanizing techniques.

According to one embodiment, the antibodies may be animal antibodies (e.g., mouse-derived antibodies), chimeric antibodies (e.g., mouse-human chimeric antibodies), humanized antibodies, or human antibodies. The antibodies may be monoclonal. The antibodies or antigen-binding fragments thereof may be isolated from a living body or non-naturally occurring. The antibodies or antigen-binding fragments thereof may be synthetic or recombinant.

An intact antibody consists of two full-length light chains and two full-length heavy chains, where each light chain is linked to the heavy chain by disulfide bonds. A constant region is present in each of the heavy and the light chains. The heavy chain constant region is of a gamma (γ), mu (μ), alpha (α), delta (δ), or epsilon (ε) type, which can be further categorized as gamma 1 (γ1), gamma 2 (γ2), gamma 3 (γ3), gamma 4 (γ4), alpha 1 (α1), or alpha 2 (α2). The light chain constant region is of either a kappa (κ) or lambda (λ) type.

As used herein, the term "heavy chain" refers to a full-length heavy chain composed of a variable region $V_H$ including an amino acid sequence sufficient to confer specificity for an antigen on the antibody, three constant region domains ($C_{H1}$, $C_{H2}$, and $C_{H3}$), a hinge, and a fragment of the full-length heavy chain. The term "light chain" refers to a full-length light chain composed of a variable region $V_L$ including an amino acid sequence sufficient to confer specificity for an antigen on the antibody, and a full-length light chain including a constant region $C_L$, or a fragment thereof The term "CDR," as used herein, refers to an amino acid sequence which resides in the heavy chain and the light chain hypervariable regions of an immunoglobulin. Each of heavy and light chains has three CDRs (CDRH1, CDRH2, CDRH3, and CDRL1, CDRL2, CDRL3). The CDRs provide contact residues that play a major role in the binding of antibodies to antigens or epitopes. As used herein, the term "specifically binding" or "specifically recognizing" has the same meaning as is well known to one of ordinary skill in the art, and indicates that an antibody and an antigen specifically interact with each other to induce an immunological activity, e.g., the binding of an antibody to an antigen inhibits the antigen's ability to bind a target (e.g., VEGFR2 or VEGFR3) or perform a function.

The term "antigen-binding fragment" refers to a fragment of the whole immunoglobulin structure which possesses a part of a polypeptide responsible for binding to antigen. Examples of the antigen-binding fragment useful in the present invention include scFv, (scFv)$_2$, scFvFc, Fab, Fab' and F(ab')$_2$, but are not limited thereto.

Of the antigen-binding fragments, Fab is composed of one variable and one constant domain from the light chain, and one variable and the first constant ($C_{H1}$) domain from the heavy chain, retaining one antigen-binding site.

A Fab' fragment is different from Fab in that the Fab' further includes a hinge region having at least one cysteine residue at the C-terminus of the heavy chain $C_{H1}$ domain.

A F(ab')$_2$ fragment forms as two Fab' fragments are coupled by a disulfide bond between the cysteine residues of the hinge region.

A Fv fragment is a minimal antibody fragment composed only of variable domains from the heavy chain and the light chain. Recombinant techniques for producing the Fv are well known in the art.

In a two-chain Fv fragment, the heavy chain variable domains are associated with the light chain variable domains via a non-covalent bond. A single-chain Fv fragment has a structure in which a heavy chain variable domain and a light chain variable domain are covalently joined to each other via a covalent bond or directly at the C-terminus, so that it can form a dimer as in a two-chain Fv fragment. In this context, the heavy chain variable region and the light chain variable region may be connected with each other through a linker, e.g., a peptide linker, or directly. The peptide linker may be composed of about 1 to about 100 amino acid residues, e.g., about 2 to about 50, about 5 to about 25, about 10 to about 40, or about 3 to about 80 amino acid residues, with no limitations imposed on the kind of the amino acid residues provided that the linker does not interfere with the function of the polypeptide. For example, the peptide linker may include Gly, Asn and/or Ser, and may also include neutral amino acids such as Thr and/or Ala. Amino acid sequences suitable for use in the peptide linker may be those well known in the art. So long as it has no negative influence on the function of the antigen-binding fragment, the length of the peptide linker may be appropriately adjusted. For example, the peptide linker may be an amino sequence composed of 1 to 100, 2 to 50, or 5 to 25 amino acid residues selected from among Gly, Asn, Ser, Thr, Ala, and a combination thereof. By way of example, the peptide linker may be (GGGGS)n (SEQ ID NO 11, wherein n represents the repeating number of (GGGGS SEQ ID. NO. 12) and may be an integer of 1 to 10, e.g., 2 to 5).

The antigen-binding fragment may be obtained using a protease (for example, a whole antibody can be digested with papain to obtain Fab fragments, or can be digested with pepsin to obtain F(ab')$_2$ fragments), or may be prepared by a genetic recombinant technique.

The term "hinge region" refers to a region that is located between $C_{H1}$ and $C_{H2}$ regions, presenting flexibility to the antigen binding site in an antibody.

When an animal-derived antibody is subjected to chimerization, an animal-derived IgG1 hinge is replaced with a human IgG1 hinge. However, the animal-derived IgG1 hinge is shorter than the human IgG1 hinge, and disulfide bonds between two heavy chains are reduced from 3 to 2, so that different effects may be elicited from the hinges due to their difference in rigidity. Therefore, modification of a hinge region can increase an antigen binding efficiency of a humanized antibody. Methods of modifying amino acid sequences of hinge regions by deleting, inserting or substituting amino acids are well known to those skilled in the art.

The anti-VEGF-C antibody may be a monoclonal antibody. Monoclonal antibodies may be prepared using a method well known in the art, for example, a phase display technique.

Meanwhile, individual monoclonal anti-annexin antibodies can be screened on the basis of their VEGF-C binding capacity using a typical Enzyme-Linked ImmunoSorbent Assay (ELISA) format. They may be analyzed for inhibitory activity using a functional assay, such as competitive ELISA for examining molecular interactions between components within a complex, and cell-based assay. Then, the monoclonal antibody members selected based on potent inhibitory activity may be tested for their respective affinities ($K_d$ values) to VEGF-C.

Another embodiment provides a pharmaceutical composition including the antagonist against VEGF-C, and/or the anti-VEGF-C antibody or an antigen-binding fragment thereof, as an active ingredient. In particular, an embodiment provides a pharmaceutical composition for inhibiting angiogenesis comprising the antagonist against VEGF-C, and/or the anti-VEGF-C antibody or an antigen-binding fragment thereof, as an active ingredient. The inhibition of angiogenesis may include not only inhibition of generation of new blood vessel but also inhibition of generation of new lymphatic vessel (lymphangiogenesis). Another embodiment provides a pharmaceutical composition for preventing and/or treating a disease associated with activation and/or overexpression of VEGF-C, including the antagonist against VEGF-C, and/or the anti-VEGF-C antibody or an antigen-binding fragment thereof, as an active ingredient.

In another embodiment, provided is a method of inhibiting angiogenesis, including administering the antagonist against VEGF-C, and/or the anti-VEGF-C antibody or an antigen-binding fragment thereof to a subject. The subject may be in need of inhibiting angiogenesis. The method of inhibiting angiogenesis may further include a step of identifying a subject who is in need of the inhibition of angiogenesis, prior to the administration step. The step of identifying may be conducted by any manners and/or methods known to relevant field for identifying whether or not a subject needs to inhibit angiogenesis or has abnormally high angiogenesis. In another embodiment, provided is a method of preventing and/or treating a disease associated with activation and/or overexpression of VEGF-C, including administering the antagonist against VEGF-C, and/or the anti-VEGF-C antibody or an antigen-binding fragment thereof to a subject. The subject may be in need of preventing and/or treating a disease associated with activation and/or overexpression of VEGF-C. The method of preventing and/or treating a disease associated with activation and/or overexpression of VEGF-C may further include a step of identifying a subject who is in need of the prevention and/or treatment of a disease associated with activation and/or overexpression of VEGF-C, prior to the administration step. The step of identifying may be conducted by any manners and/or methods known to relevant field for identifying whether or not a subject needs prevention and/or treatment of a disease associated with activation and/or overexpression of VEGF-C. For example, the step of identifying may include diagnosing a subject as a patient with a disease associated with activation and/or overexpression of VEGF-C, or identifying a subject who has been diagnosed as having a disease associated with activation and/or overexpression of VEGF-C. In the methods, the antagonist against VEGF-C, and/or the anti-VEGF-C antibody or an antigen-binding fragment thereof may be administered in amount that is pharmaceutically effective, which amount may be determined by the skilled medical practitioner or medical researcher.

The antagonist against VEGF-C, the anti-VEGF-C antibody or an antigen-binding fragment thereof, or the pharmaceutical composition as described above may be formulated in combination with a pharmaceutically acceptable carrier. So long as it is usually used in drug formulations, any pharmaceutically acceptable carrier may be contained in the pharmaceutical composition. Examples of the pharmaceutically acceptable carrier available for the pharmaceutical composition of the present invention include lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto. In addition to the carrier, the pharmaceutical composition may further include a typical additive selected from the group consisting of a diluent, an excipient, a lubricant, a humectant, a sweetener, a flavor enhancer, an emulsifier, a suspending agent, a preservative, and a combination thereof.

The antagonist against VEGF-C, the anti-VEGF-C antibody or an antigen-binding fragment thereof, or the pharmaceutical composition may be administered orally or parenterally. For parenteral administration, the administration may be carried out via intravenous, subcutaneous, intramuscular, intraperitoneal, intradermal, local, intranasal, intrapulmonary, and intrarectal routes, but is not limited thereto. For oral administration, however, the pharmaceutical composition is preferably coated or formulated to protect the active ingredient from being degraded in the stomach because proteins or peptides are digested by pepsin. In addition, the administration may be performed with the aid of an instrument adapted for delivering the pharmaceutical composition to target cells.

The content of the anti-VEGF-C antibody or an antigen-binding fragment thereof in the pharmaceutical composition may be determined in consideration of various factors including the type of formulation the patient's age, weight, and sex, the severity of the disorder being treated, diet, the time of administration, the route of administration, the rate of excretion, and sensitivity. For example, the daily dose of the anti-VEGF-C antibody or its antigen-binding fragment may be on the order of about 0.001 to about 1000 mg/kg, particularly on the order of about 0.01 to about 100 mg/kg, and more particularly on the order of about 0.1 to about 50 mg/kg, but is not limited thereto. A daily dose may be formulated into a unit dose form or distributed into separate dose forms, or may be included within a multiple dose package.

The term "pharmaceutically effective amount," as used herein, refers to an amount at which the active ingredient (e.g., the anti-VEGF-C antibody or an antigen-binding fragment thereof) can exert a desired effect, that is, a prophylactic and/or therapeutic effect on a disease associated with VEGF-C activation and/or overexpression, and may vary depending on various factors including the type of formulation, the patient's age, weight, and sex, the severity of the disorder being treated, diet, the time of administration, the route of administration, the rate of excretion, and sensitivity.

The subject to be administered with the antagonist against VEGF-C, the anti-VEGF-C antibody or an antigen-binding fragment thereof, or the pharmaceutical composition may an mammal examples of which include primates such as humans or a monkeys, and rodents such as rats and mice, or cells or tissue separated therefrom, but are not limited thereto.

The antagonist against VEGF-C, the anti-VEGF-C antibody or an antigen-binding fragment thereof, or the pharmaceutical composition may be formulated into solutions in oil or aqueous media, suspensions, syrup, emulsions, elixirs, powders, granules, tablets, or capsules, and in this context, a dispersant or a stabilizer may be further employed.

Particularly, the pharmaceutical composition including the anti-VEGF-C antibody or an antigen-binding fragment thereof can be formulated into immunoliposomes. Liposomes including an antibody can be prepared using methods that are well-known in the art. The immunoliposomes may be produced from a lipid composition including phosphatidylcholine, cholesterol, and PEGylated phosphatidylethanolamine by reverse-phase evaporation. To quote an example, Fab' can be conjugated to liposomes by disulfide reformation.

Since the antagonist against VEGF-C, the anti-VEGF-C antibody or an antigen-binding fragment thereof is capable of specifically binding to VEGF-C, the antagonist against VEGF-C, or the anti-VEGF-C antibody or an antigen-binding fragment thereof can be applicable to the detection of VEGF-C or the determination of VEGF-C activation and/or overexpression.

Accordingly, another embodiment provides a composition for the detection of VEGF-C, including the antagonist against VEGF-C, and/or the anti-VEGF-C antibody or an antigen-binding fragment thereof. Another embodiment provides a method for detecting VEGF-C, including applying the antagonist against VEGF-C and/or the anti-VEGF-C antibody or an antigen-binding fragment thereof to a biological sample; and measuring an antigen-antibody reaction (binding; for example to form a complex) in the biological sample. In the detecting method, VEGF-C is determined to exist in the biological sample if the antigen-antibody reaction is detected. The biological sample may be selected from among cells, tissues, and body fluids (e.g., blood, serum, etc.) isolated from mammals including primates such as humans and monkeys, and rodents such as mice and rats. The detection of VEGF-C is accounted for by examining whether and to what extent VEGF-C exists and is expressed.

Another embodiment provides a pharmaceutical composition for determining VEGF-C activation and/or overexpression, and/or diagnosing a disease associated with activation and/or overexpression of VEGF-C, including the antagonist against VEGF-C, and/or the anti-VEGF-C antibody or an antigen-binding fragment thereof. Another embodiment provides a method for determining VEGF-C activation and/or overexpression, and/or diagnosing a disease associated with VEGF-C activation and/or overexpression, including applying the antagonist against VEGF-C and/or the anti-VEGF-C antibody or an antigen-binding fragment thereof to a biological sample from a subject; and measuring an antigen-antibody reaction (binding; for example to form a complex) in the biological sample. In this method, the biological sample or the subject from which the biological sample is obtained is determined to have VEGF-C activation and/or overexpression or a disease associated with VEGF-C activation and/or overexpression if the antigen-antibody reaction in the biological sample is detected at a higher level than that in a normal sample (i.e., a sample known to have normal VEGF-C levels). Accordingly, the method may further include applying the antagonist against VEGF-C and/or the anti-VEGF-C antibody or an antigen-binding fragment thereof to a normal sample; and measuring an antigen-antibody reaction (binding) in the normal sample. Alternatively, the level of antigen-antibody (or antigen-antagonist) binding may be a predetermined value that represents the level in a normal sample or group of normal samples.

The biological sample may be selected from among cells, tissues, and body fluids (e.g., blood, serum, etc.) isolated from a subject in suspicion. The normal sample may be selected from among cells, tissues, and body fluids (e.g., blood, serum, etc.) obtained (isolated) from a subject which is identified as being free of VEGF-C activation and/or overexpression, and/or a disease associated with VEGF-C activation and/or overexpression. The subject may be a mammal selected from among primates including humans and monkeys, and rodents including mice and rats.

The measurement of the biological sample for an antigen-antibody reaction may be carried out using a method well known in the art, for example, on the basis of an enzyme reaction, fluorescence, luminescence, and/or radiation. Examples of the method useful for examining the antigen-antibody reaction of the biological sample may include immune-chromatography, immunohistochemistry, enzyme linked immunosorbent assay (ELISA), radioimmunoassay (RIA), enzyme immunoassay (EIA), fluorescence immunoassay (FIA), luminescence immunoassay (LIA), and Western blotting, but are not limited thereto.

The disease associated with VEGF-C activation and/or overexpression may be selected from the group consisting of cancers; cancer metastasis; cancer invasion or infiltration; eye disorders such as macular degeneration (e.g., age-related macular degeneration), diabetic retinopathy and the like; inflammatory disease such as psoriasis, rheumatic arthritis, chronic inflammation, sepsis, and the like; malaria; and the like. The cancer may be related to overexpression of VEGF-C, and may be a solid cancer or blood cancer. For example, the cancer may be one or more selected from the group consisting of squamous cell carcinoma, small-cell lung cancer, non-small-cell lung cancer, adrenocarcinoma of lung, squamous cell carcinoma of lung, peritoneal cancer, skin cancer, skin or intraocular melanoma, rectal cancer, perianal cancer, esophagus cancer, small intestine cancer, endocrine gland cancer, parathyroid cancer, adrenal cancer, soft-tissue sarcoma, urethral cancer, chronic or acute leukemia, lymphocytic lymphoma, hepatoma, gastrointestinal cancer, gastric cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, head or neck cancer, brain cancer, osteosarcoma, and a combination thereof. In a specific embodiment, the cancer may be non-small-cell lung cancer and/or pancreatic cancer. The cancer may include a primary cancer or a metastatic cancer.

Another embodiment provides a polynucleotide encoding a polypeptide which comprises or consists essentially of at least one selected from the amino acid sequences of SEQ ID NO: 1 to SEQ ID NO: 6, or the antagonist, or the antibody, as described above. In an particular embodiment, the polynucleotide may encode a polypeptide including the amino acid sequence of SEQ ID NO: 7, the amino acid sequence of SEQ ID NO: 8, or a combination thereof. Another embodiment provides a recombinant vector carrying (comprising) the polynucleotide. Another embodiment provides a recombinant cell transformed with the recombinant vector.

The term "vector" refers to a means for expressing a target gene in a host cell, as exemplified by a plasmid vector, a cozmid vector, and a viral vector such as a bacteriophage vector, adenovirus vector, retrovirus vector, and an adeno-related virus vector. The recombinant vector may be constructed from, but not limited to, well-known plasmids (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, pUC19, etc.), phages (for example, λgt4λB, λ-Charon, λΔz1, M13, etc.) or viruses (for example, SV40, etc.) by manipulation.

In the recombinant vector, the polynucleotide may be operatively linked to a promoter. The term "operatively linked" is intended to pertain to a functional linkage between a nucleotide sequence of interest and an expression regulatory element (for example, a promoter sequence) so that the expression of the nucleotide sequence of interest is governed by the regulatory element. For instance, when it is "operatively linked" to the regulatory element, the nucleotide sequence of interest can be transcribed and/or translated under the control of the regulatory element.

The recombinant vector may be constructed typically as a cloning vector or an expression vector. For recombinant expression vectors, a vector typically available for expressing a foreign protein in plant, animal or microorganism cells may be employed. Various methods well known in the art may be used for the construction of recombinant vectors.

For use in hosts, such as prokaryotic or eukaryotic cells, the recombinant vector may be constructed appropriately. For example, when a vector is constructed as an expression vector for use in a prokaryotic host, the vector typically includes a strong promoter for transcription (e.g., a pLλ promoter, a CMV promoter, a trp promoter, a lac promoter, a tac promoter, a T7 promoter, etc.), a ribosomal binding side for initiating translation, and transcriptional/translational termination sites. On the other hand, an expression vector for use in a eukaryotic host includes an origin of replication operable in a eukaryotic cell, such as a f1 origin of replication, an SV40 origin of replication, a pMB1 origin of replication, an adeno origin of replication, an AAV origin of replication, a BBV origin of replication. In addition, the expression vector typically includes a promoter derived from mammalian cells (for example, metallothionein promoter) or from mammalian viruses (for example, adenovirus late promoter, vaccinia virus 7.5K promoter, SV40 promoter, cytomegalovirus promoter and tk promoter of HSV), and a polyadenylation sequence as a transcription termination sequence.

The recombinant cell may be prepared by introducing the recombinant vector into a suitable host cell. So long as it allows for the sequential cloning and expression of the recombinant vector in a stable manner, any host cell known in the art may be employed in the present invention. Examples of the prokaryotic host cell available for the present invention include *E. coli* JM109, *E. coli* BL21, *E. coli* RR1, *E. coli* LE392, *E. coli* B, *E. coli* X 1776, *E. coli* W3110, *Bacillus* spp. such as *Bacillus subtilis* and *Bacillus thuringiensis*, and enterobacteriaceae strains such as *Salmonella typhimurium, Serratia marcescens* and various *Pseudomonas* species. Eukaryotic host cells to be transformed may be *Saccharomyces cerevisiae*, insect cells, and animal cells including, but not limited to, Sp2/0, CHO (Chinese hamster ovary) K1, CHO DG44, PER.C6, W138, BHK, COS-7, 293, HepG2, Huh7, 3T3, RIN, and MDCK.

Using a method well known in the art, the polynucleotide or a recombinant vector carrying the polynucleotide may be introduced (incorporated) into a host cell. This transformation is carried out through $CaCl_2$ or electroporation when the host cell is prokaryotic. For eukaryotic host cells, the genetic introduction may be achieved using, but not limited to, microinjection, calcium phosphate precipitation, electroporation, liposome-mediated transfection, or particle bombardment.

To select a transformed host cell, advantage may be taken of the phenotype attributed to a selection marker according to a method known in the art. For example, when the selection marker is a gene resistant to a certain antibiotic, the host cells may be grown in the presence of the antibiotic in a medium to select a transformant of interest.

The polypeptide, antagonist, antibody, or antibody fragment described herein can be prepared (manufactured) by any suitable method, for instance, by expressing a polynucleotide encoding the polypeptide, antagonist, antibody, or antibody fragment in a cell (for example, by culturing a cell comprising a polynucleotide encoding the polypeptide, antagonist, antibody, or antibody fragment under suitable conditions). The cell produces the polypeptide, antagonist, antibody, or antibody fragment, which can be harvested from the cell or the cell culture medium.

EXAMPLES

Hereafter, the present invention will be described in detail by examples.

The following examples are intended merely to illustrate the invention and are not construed to restrict the invention.

Example 1

Preparation of a Human Anti-VEGF-C Antibody

An fully human anti-VEGF-C antibody was prepared using phage display scFv library (obtained from Ewha University Industry Collaboration Foundation; Korea) and human VEGF-C polypeptide (R&D systems; Human VEGF-C; Accession # P49767(hVEGF-C)). Detailed protocol was as follows:

The human VEGF-C polypeptide was plated on MaxiSorp™ immunotube (Nunc) at the amount of about 10 μg (microgram)/ml, about 1 μg/ml, or about 0.1 μg/ml, and phage particles that bind to VEGF-C were enriched through primary, secondary, and tertiary panning. The surface of the immunotube was blocked using about 3%(v/v) milk in phosphate buffer saline (PBS). Then, about $1 \times 10^{12}$ of phage particles derived from the phage display scFv library were added to 0.5 mL of 3%(v/v) milk, and incubated at 37° C. for 1 hour, to be blocked. Then, the phage particles that were blocked with milk were added to the immunotube that was coated with VEGF-C, and incubated at room temperature for 1 hour.

After the incubation of the phage, the surfaces of the phages were washed 3~5 times with PBS containing 0.1% (v/v) of Tween 20, and then, the bound phages were eluted using 100 mM triethanolamine. The eluted phages were transfected into *E. coli* ER2537 cells (New England Biolabs., USA), amplified, and then collected, to be provided for the use of the following screening step. VEGF-C polypeptide was plated on MaxiSorp™ immunotube (Nunc) at the amount of about 10 μg (microgram)/ml, about 1 μg/ml, or about 0.1 μg/ml, and the above process was repeated three times. As a result, about 600 specific VEGF-C-binding scFv clones which recognized human VEGF-C (Accession # P49767) were identified through ELISA (Enzyme-Linked ImmunoSorbent Assay) affinity test (refer to Example 2).

Example 2

Selection of Anti-VEGF-C Antibody Producing Clones and Purification of the Antibody Finally, 20 clones were generated from ~600 VEGF-C-binding scFv clones obtained from Example 1, based on the binding strength to VEGF-C. Specifically, clones were tested for their binding strength to VEGF-C and inhibitory capacity in the binding of VEGF-C to VEGR-R3. Through these processes, the several clones showing high ELISA OD value were selected. The selected clones were then incubated in SB media (BD Bioscience) supplemented with ampicillin until the OD 600 value reaches 1.0 (OD 600=1.0), and 1 mM IPTG (Isopropyl-β-D-Thiogalactopyranoside) was added to induce the expression of the scFv clones. The periplasm fractions from the infected *E. coli* were collected, and an anti-VEGF-C scFv antibody was partially purified using NI-NTA column (QIAGEN).

Example 3

VEGF-C:VEGR-R3 Neutralization ELISA (Competitive ELISA) Using the Anti-VEGF-C Antibody in scFv Form To examine the effect of the anti-VEGF-C antibody purified in Example 2 on the inhibition of VEGF-C:VEGR-R3 binding, a competitive ELISA, which is used for verification of molecular interaction, was performed. MaxiSorp™ flat-bottom plate (Nunc) of 96-wells was coated with 2 μg/μl of human VEGR-R3-Fc (R&D Systems. Accession No. P35916) which is a fusion protein composed of human VEGR-R3 and Fc of human IgG1. Thereafter, the plate was washed 5 times with phosphate buffer saline (PBS) supplemented with 0.05%(v/v) Tween-20, and then blocked with PBS supplemented with 1%(v/v) bovine serum albumin (BSA; Sigma) at room temperature for 2 hours.

To perform the VEGF-C:VEGR-R3 neutralization ELISA, the anti-VEGF-C antibody (concentration: 1 nM, 10 nM, 100 nM, or 1000 nM) purified in Example 2 was added to each well coated with the human VEGR-R3-Fc, together with a mixture of 1%(v/v) BSA and 200 ng/ml of FLAG-tagged human VEGF-C (Accession # P49767), and incubated at room temperature for 2 hours. Thereafter, the plate was washed 5 times with PBS supplemented with 0.05% (v/v) Tween-20. HRP-conjugated anti-FLAG antibody (SIGMA) diluted with PBS supplemented with 1%(v/v) BSA at the dilution ratio of 1:5,000 (v/v) was added to each well in the amount of 100 μl and incubated at room temperature for 1 hour. The reacted well was washed 5 times with PBS supplemented with 0.1%(v/v) Tween-20. Finally, tetramethylbenzidine (TMB) substrate (Cell Signal) was added to each well of the plate at the amount of 100 μl to induce coloring reaction at room temperature for 3 minutes. Then, the reaction was stopped by addition of 50 μl of 5N $H_2SO_4$ solution, and OD450 value was measured using plate reader (Molecular Devices). 50% inhibition concentration (IC50) for VEGF-C:VEGR-R3 binding affinity was calculated which is summarized in Table 2.

TABLE 2

| Antibody | 50% inhibition concentration for VEGF-C:VEGR-R3 binding affinity (IC50, nM) |
|---|---|
| SAIT-VEGFC-AB-4A2 | 33.36 |

In Tables 2-5 and 7, the anti-VEGF-C antibody in scFv form purified in Example 2 is named as "SAIT-VEGFC-AB-4A2".

As shown in Table 2, the anti-VEGF-C antibody can neutralize the binding affinity between VEGF-C and VEGR-R3.

Example 4

ELISA to Verify Binding to Human VEGF-C

ELISA for verifying the binding affinity of the anti-VEGF-C antibody in scFv form purified in Example 2 to its antigen was carried out. MaxiSorp™ flat-bottom plate (Nunc) of 96-wells was coated with 1 μg/ml of human VEGF-C(R&D Systems) for 16 hours. The plate was then washed 5 times with phosphate buffer saline (PBS) supplemented with 0.05%(v/v) Tween-20, and then blocked with PBS supplemented with 1%(v/v) bovine serum albumin (BSA; Sigma) at room temperature for 2 hours. The anti-VEGF-C antibody in scFv form purified in Example 2 was added to each well of the plate and was incubated at room temperature for 2 hours.

The plate was washed 5 times with PBS supplemented with 0.05% (v/v) Tween-20. HRP-conjugated anti-HA antibody (HA-probe Antibody (F-7) HRP conjugated) (Santacruz) diluted with PBS supplemented with 1%(v/v) BSA was added at the dilution ratio of 1:1,000 (v/v) and was incubated at room temperature for 1 hour. The reacted well was washed 5 times with PBS supplemented with 0.1%(v/v) Tween-20. Finally, tetramethylbenzidine (TMB) substrate (Cell Signal) was added to each well of the plate at the amount of 100 μl to induce coloring reaction at room temperature for 3 minutes. Then, the reaction was stopped with 50 μl of 5N $H_2SO_4$ solution, and OD450 value was measured on plate reader (Molecular Devices). By obtaining 50% binding concentration (Kd) to human VEGF-C, the binding affinity of the anti-VEGF-C antibody to the VEGF-C protein was measured. The obtained results are shown in Table 3:

TABLE 3

| Antibody | 50% binding concentration to human VEGF-C (Kd, nM) |
|---|---|
| SAIT-VEGFC-AB-4A2 | 26.2 |

Example 5

Cloning of Gene Encoding the Human Anti-VEGF-C Antibody

The gene sequences encoding the heavy chain and light chain variable regions of the monoclonal antibody of Example 2 were amplified using a primer set (PC3X Reverse Primer: 5'-AAC CAT CGA TAG CAG CAC CG-3' SEQ ID. NO: 13 PC3X Forward primer: 5'-GCA CGA CAG GTT TCC CGA-3' SEQ ID. NO: 14 in the below condition:

PCR condition:

at 94° C. for 5 minutes;

[at 94° C. for 1 minute, at 55° C. for 1 minute, at 72° C. for 2 minutes] ×30cycles;

at 72° C. for 6 minutes;

cooling to 4° C.

The PCR products from each reactant were purified using QIAquick Multiwell PCR Purification kit (Qiagen) according to manufacturer's manual.

After cloning the obtained PCR products, the DNA sequences thereof were analyzed by a publicly known method. As a result, the amino acid sequences of CDRs, SEQ ID NO: 7 (heavy chain variable region), and SEQ ID NO: 8 (light chain variable region) as shown in Tables 4 and 5, were obtained.

TABLE 4

| Amino Acid Sequence of Heavy Chain | | | |
|---|---|---|---|
| antibody | CDRH1-KABAT | CDRH2-KABAT | CDRH3-KABAT |
| SAIT-VEGFC-AB-4A2 | SYDMS (SEQ ID NO: 1) | AISYDNGSTYYADSVKG (SEQ ID NO: 2) | ARDPYLARLNTFDY (SEQ ID NO: 3) |

TABLE 5

| Amino Acid Sequence of Light Chain | | | |
|---|---|---|---|
| antibody | CDRL1-KABAT | CDRL2-KABAT | CDRL3-KABAT |
| SAIT-VEGFC-AB-4A2 | SGSSSNIGSNNVS (SEQ ID NO: 4) | YNSHRPS (SEQ ID NO: 5) | ATWDSSLNG (SEQ ID NO: 6) |

Example 6

Expression and Purification of Intact Antibody

Each of the nucleotide sequences of SEQ ID NO: 9 encoding the heavy chain variable region (SEQ ID NO: 7) and SEQ ID NO: 10 encoding the light chain variable region (SEQ ID NO: 8) was cloned into a different vector from each other. The nucleotide sequence encoding the heavy chain variable region was cloned into pOPTI-VAC (Invitrogen) which is a vector including cytomegalovirus (CMV) promoter, human IgG1 constant region, and Fc region. The nucleotide sequence encoding the light chain variable region was cloned into pFUSE2-CLIg-h12 (Invivogen) which is a vector including CMV promoter and human IgG1 constant region.

In particular, the heavy chain variable region and the vector including the heavy chain variable region were treated with restriction enzymes, corI(neb) and NheI(neb), and the light chain variable region and the vector including the light chain variable region were treated with restriction enzymes, ecorI(neb) and avrII(neb). Then, they were subjected to ligation with T4 DNA Ligase (New England Biolab), to obtain a heavy chain vector and a light chain vector for expression of an antibody including the desired variable regions.

The obtained heavy chain vector and the light chain vector were transfected together into 293-F cells (Invitrogen). The cells were cultured in serum-free 293-f expression medium (Invitrogen), and at $5^{th}$ day, the culture solution was collected. The obtained culture solution included an expressed antibody consisting of the heavy chain including the variable region of SEQ ID NO: 7 and the light chain including the variable region of SEQ ID NO: 8. The antibody-contained culture solution was centrifuged at 1000×g to remove remained cells and impurities, and then, subjected to an affinity chromatography using Protein A (GE-Healthcare) which has strong affinity to Fc region of antibody and low PH elution, thereby purifying an anti-VEGF-C antibody in IgG form.

Example 7. VEGF-C: VEGF-R3 neutralization ELISA (Competitive ELISA) Using the Anti-VEGF-C Antibody in IgG Form To examine the inhibitory effect of the anti-VEGF-C antibody in IgG form purified in Example 6 on the interaction between VEGF-C:VEGR-R3, a neutralization ELISA (competitive ELISA), which is used for verification of molecular interaction, was performed.

MaxiSorp™ flat-bottom plate (Nunc) of 96-wells was coated with 2 μg/μl of human VEGR-R3-Fc (R&D Systems. Accession No. P35916) which is a protein produced by coupling human VEGR-R3 with Fc of human IgG1. Thereafter, the plate was washed 5 times with phosphate buffer saline (PBS) supplemented with 0.05%(v/v) Tween-20, and then blocked with PBS supplemented with 1%(v/v) bovine serum albumin (BSA; Sigma) at room temperature for 2 hours.

For performing the VEGF-R3:VEGF-C neutralization ELISA, the anti-VEGF-C antibody (concentration: 1 nM, 10 nM, 100 nM, or 1000 nM) in IgG form purified in Example 6 was added to each well of the human VEGR-R3-Fc coated plate, together with a mixture of 1%(v/v) BSA and 200 ng/ml of FLAG-tagged human VEGF-C (Accession # P49767), and then, the plate was reacted at room temperature for 2 hours. Thereafter, the plate was washed 5 times with PBS supplemented with 0.05% (v/v) Tween-20. HRP-conjugated anti-FLAG antibody (SIGMA) was diluted with PBS supplemented with 1%(v/v) BSA at the dilution ratio of 1:5,000 (v/v), and added to each well in the amount of 100 μl, to react at room temperature for 1 hour. The reacted well was washed 5 times with PBS supplemented with 0.1%(v/v) Tween-20. Finally, tetramethylbenzidine (TMB) substrate (Cell Signal) was added to each well of the plate at the amount of 100 μl, to induce coloring reaction at room temperature for 3 minutes. Then, the reaction was stopped with 50 μl of 5N $H_2SO_4$ solution, and OD450 value was measured on plate reader (Molecular Devices). Through the results, 50% inhibition concentration (IC50) for VEGF-C: VEGR-R3 binding affinity was obtained, and summarized in Table 6.

TABLE 6

| Antibody | 50% inhibition concentration for VEGF-C:VEGR-R3 binding affinity (IC50, nM) |
|---|---|
| SAIT-VEGFC-AB-4A2 | 9.2 |

In Table 6, the anti-VEGF-C antibody in IgG form purified in Example 6 is also named as "SAIT-VEGFC-AB-4A2".

As shown in Table 6, the anti-VEGF-C antibody can neutralize the binding affinity between VEGF-C and VEGR-R3.

Example 8

Cell Proliferation Inhibition Effect of the Anti-VEGF-C Antibody in IgG Form

The cell proliferation level was measured by an analysis using cell counting kit-8 (Dojindo Molecular Technology). Human lymphatic endothelial cells (HLEC; ATCC) of P5-P7 were added to collagen coated 96 well plate (BD Bioscience) at the amount of 3000~5000 cells/well, and cultured. 2 μg/ml of VEGF-C (P49767) and 1% BSA were mixed with EBM-2 (Lonza), and the anti-VEGF-C antibody in IgG form purified in Example 6 was added to the obtained mixture at a concentration of 1, 10, or 100 μg/ml. After removing the supernatant from the 96-well plate, the plate was washed with PBS, added with the medium including the mixture of VEGF-C and anti-VEGF-C antibody, and cultured for 3 days. To analyze the cell proliferation, 10 μl of CCK-8 solution (Dojindo) was added to the cell culture, allowing further culture for 1 hour, and then, the absorbance at 450 nm was read using Microplate reader (Perkin Elmer).

The obtained results are illustrated in FIG. 1. As shown in FIG. 1, it is confirmed that the proliferation of lymphatic endothelial cells by VEGF-C is inhibited by the anti-VEGF-C antibody.

Example 9

Cell Migration Inhibition Effect of the Anti-VEGF-C Antibody in IgG Form

The cell migration of endothelial cells (ECs) and lymphatic endothelial cells (LECs) was measured by a cell migration assay using xCelligence Realtime cell analyzer; GE Healthcare (RTCA). The RTCA is a non-invasive cell monitoring system capable of examining the change in cell number by measuring the impedance in real-time. To conduct the cell migration assay, CIM-plate16 (GE Healthcare) including lower chamber and upper chamber was used, wherein microelectrodes for measuring the impedance are arranged in the upper chamber, and when the cells migrate through the micro holes, the migrated cells attach to the microelectrodes, thereby examining the cell migration level, and the cell migration level can be converted into migration index. Endothelial cells (EC; ATCC) and lymphatic endothelial cells (LEC; Lonza) which were cultured in EGM-2 medium (Lonza) were cultured in EBM medium supplemented with 1% FBS for 6 hours. 0.5 μg/ml or 1 μg/ml of VEGF-C and 10 μg/ml or 20 μg/ml of the anti-VEGF-C antibody were added to 2%(v/v) FBS contained EBM medium (Lonza) in each well of lower chamber of CIM-plate16, and then, fibronectin (Sigma) coated upper chamber was assembled therewith. 30 μl of serum-free EBM medium was added to the upper chamber, and left in incubator for 1 hour for equilibration between the plate and the medium. Then, the CIM-plate was equipped in device station in the incubator, and background value was measured. Lymphatic endothelial cells (LEC; ATCC) which were re-suspended with serum-free media were seeded at the amount of 60,000 cells/well, left for 15 minutes so that they can settle down, and applied to the device, to measure the cell migration in real time. The cell migration level was expressed by slope (1/hr: the rate of cell proliferation or migration, which is obtained by measuring the impedance per time in a well containing cells).

Figure 2:
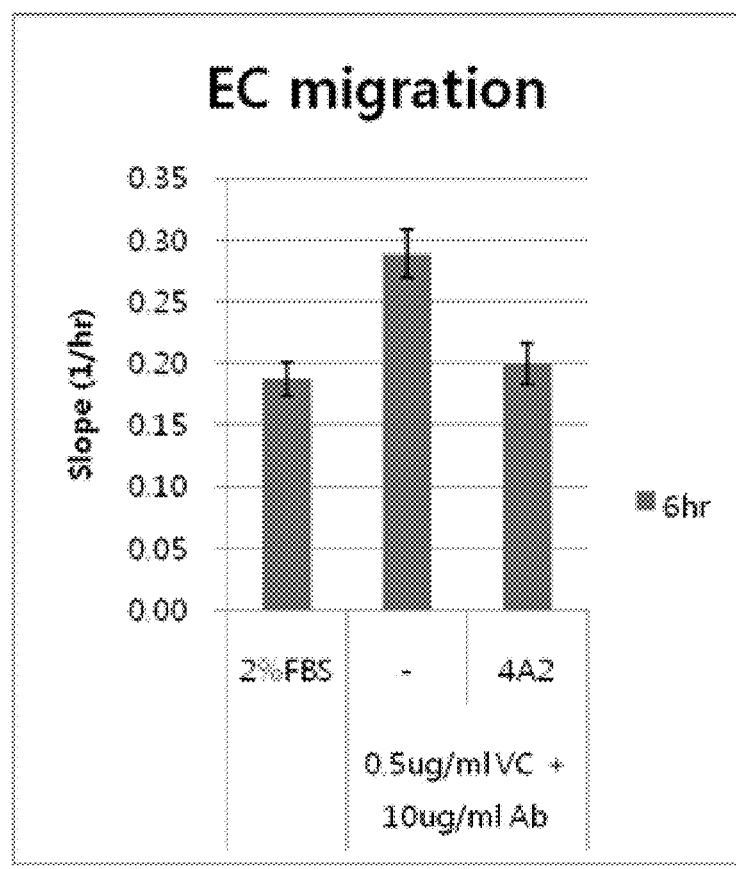
FIG. 2 is a graph displaying the migration degree of endothelial cells (ECs) when treated with an anti-VEGF-C antibody according to one embodiment, wherein the Y-axis (slope) indicates the rate of cell proliferation or migration.
Figure 3:
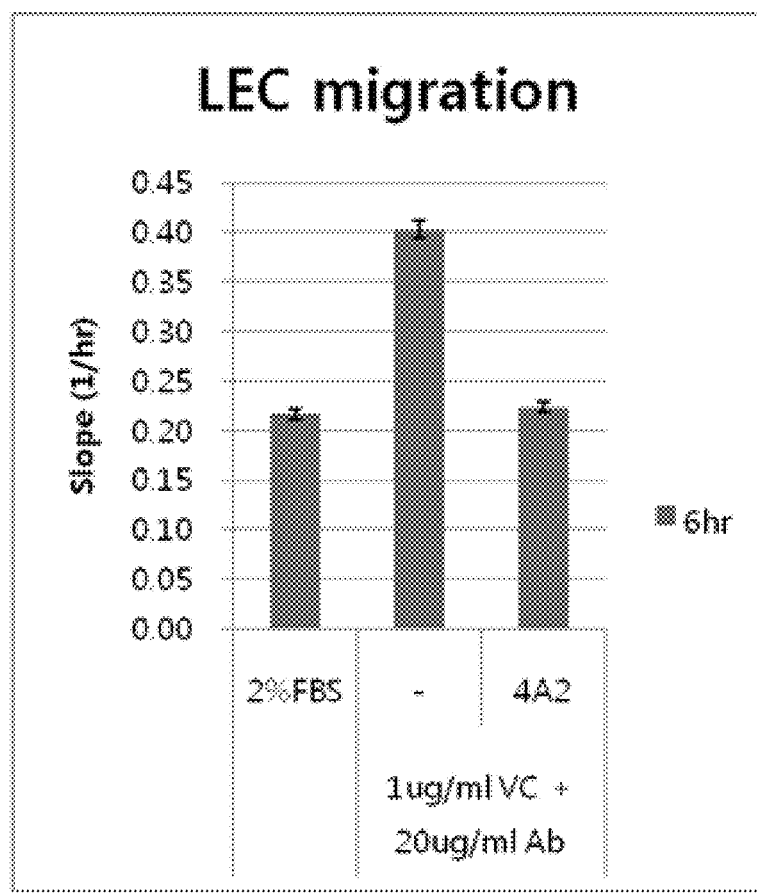
FIG. 3 is a graph displaying the migration degree of LECs when treated with an anti-VEGF-C antibody according to one embodiment, wherein the Y-axis (slope) indicates the rate of cell proliferation or migration.

The obtained results are illustrated in FIGS. 2 (EC) and 3 (LEC). As shown in FIGS. 2 and 3, the cell migrations of ECs and LECs, which are increased by VEGF-C, are inhibited by the anti-VEGF-C antibody.

Example 10

Measurement of Antigen Affinity (Kd Values) Using Surface Plasmon Resonance (SPR)

To accurately measure the affinity of the anti-VEGF-C antibody to its antigen, VEGF-C, Surface Plasmon Resonance (SPR) method was conducted using BIAcore T100 (GE Healthcare). The SPR method is based on a principle that the refractive index of light passing through a sensor chip varied depending on the condition of the substance coated on the sensor chip. If an antibody or an antigen is flowed on the chip which is coated with an antigen or an antibody, the binding between the antigen and the antibody leads to change in refractive index, and Kd value can be calculated based on the refractive index.

25 μg/ml of anti-human Fc antibody (Sigma) was fixed on CM5 sensor chip (GE Healthcare) using pH 5.0 sodium acetate solution and amine coupling kit (GE Healthcare). 2 μg/ml of the anti-VEGF-C antibody obtained in Example 2 was added on the chip to be captured.

Recombinant VEGF-C protein (R&D Systems) was serially diluted with HBS-P (GE-Health) solution starting from the concentration of 200 nM and flowed on the chip, leading to binding (on) to and dissociating (off) from the antibody, thereby measuring the antigen-antibody affinity.

The obtained results are summarized in Table 7:

TABLE 7

| antibody | On rate (1/Ms) | Off Rate (1/s) | Affinity (Kd, M) |
|---|---|---|---|
| SAIT-VEGFC-AB-4A2 | $7.454 \times 10^6$ | 0.002575 | $3.454 \times 10^{-10}$ |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-VEGF-C antibody or an antigen binding fragment thereof comprising:
a CDR-H1 comprising the amino acid sequence of SEQ ID NO: 1, a CDR-H2 comprising the amino acid sequence of SEQ ID NO: 2, a CDR-H3 comprising the amino acid sequence of SEQ ID NO: 3, a CDR-L1 comprising the amino acid sequence of SEQ ID NO: 4, a CDR-L2 comprising the amino acid sequence of SEQ ID NO: 5, and a CDR-L3 comprising the amino acid sequence of SEQ ID NO: 6;
wherein the anti-VEGF-C antibody or an antigen binding fragment thereof binds VEGF-C.

2. The anti-VEGF-C antibody or an antigen binding fragment thereof of claim 1, wherein the anti-VEGF-C antibody or an antigen binding fragment thereof is an anti-VEGF-C peptibody, an anti-VEGF-C nanobody, or a combination thereof.

3. The anti-VEGF-C antibody or an antigen binding fragment thereof of claim 1, wherein the antigen-binding fragment is an scFv, (scFv)2, scFv-Fc, Fab, Fab', or F(ab')2.

4. The anti-VEGF-C antibody or an antigen binding fragment thereof of claim 1, wherein the anti-VEGF-C antibody or an antigen-binding fragment thereof is synthetic or recombinant.

5. The anti-VEGF-C antibody or an antigen binding fragment thereof of claim 1, wherein the anti-VEGF-C antibody or antigen binding fragment thereof is monoclonal.

6. A method of preventing or treating a disease associated with activation or overexpression of VEGF-C in a subject, comprising
administering the anti-VEGF-C antibody or an antigen binding fragment thereof C of claim 1 to the subject, thereby preventing or treating a disease associated with activation or overexpression of VEGF-C in the subject.

7. The method of claim 6, wherein the anti-VEGF-C antibody or an antigen-binding fragment thereof comprises a heavy chain variable region comprising SEQ ID NO: 7, and a light chain variable region comprising SEQ ID NO: 8.

8. The method of claim 6, wherein the anti-VEGF-C antigen-binding fragment is an scFv, (scFv)2, scFv-Fc, Fab, Fab', or F(ab')2.

9. The method of claim 6, wherein the anti-VEGF-C antibody or an antigen-binding fragment thereof is synthetic or recombinant.

10. The method of claim 6, wherein the anti-VEGF-C antibody or antigen binding fragment thereof is monoclonal.

11. An anti-VEGF-C antibody or an antigen binding fragment thereof comprising:
a heavy chain variable region comprising the amino acid sequence of SEQ ID NO: 7, and a light chain variable region comprising the amino acid sequence of SEQ ID NO: 8,
wherein the anti-VEGF-C antibody or an antigen binding fragment thereof binds VEGF-C.

* * * * *

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Synthetic (a polypeptide capable of being used
      as a CDR-H1 of an anti-VEGF-C antibody)

<400> SEQUENCE: 1

Ser Tyr Asp Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic (a polypeptide capable of being used
      as a CDR-H2 of an anti-VEGF-C antibody)

<400> SEQUENCE: 2

Ala Ile Ser Tyr Asp Asn Gly Ser Thr Tyr Tyr Ala Asp Ser Val Lys
1               5                   10                  15

Gly

<210> SEQ ID NO 3
<211> LENGTH: 14
<212> TYPE: PRT
<213> ORGANISM: Artificial Sequence
<220> FEATURE:
<223> OTHER INFORMATION: Synthetic (a polypeptide capable of being used
      as a CDR-H3 of an anti-VEGF-C antibody)

<400> SEQUENCE: 3

Ala Arg Asp Pro Tyr Leu Ala Arg Leu Asn Thr Phe Asp Tyr
1               5                   10

<210> SEQ ID NO 4
<211> LENGTH: 13
<212> TYPE: PRT
<213> ORGANISM: Artificial Sequence
<220> FEATURE:
<223> OTHER INFORMATION: Synthetic (a polypeptide capable of being used
      as a CDR-L1 of an anti-VEGF-C antibody)

<400> SEQUENCE: 4

Ser Gly Ser Ser Ser Asn Ile Gly Ser Asn Asn Val Ser
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic (a polypeptide capable of being used
      as a CDR-L2 of an anti-VEGF-C antibody)

<400> SEQUENCE: 5

Tyr Asn Ser His Arg Pro Ser
1               5

<210> SEQ ID NO 6
<211> LENGTH: 9
<212> TYPE: PRT
<213> ORGANISM: Artificial Sequence
```

```
<220> FEATURE:
<223> OTHER INFORMATION: Synthetic (a polypeptide capable of being used
      as a CDR-L3 of an anti-VEGF-C antibody)

<400> SEQUENCE: 6

Ala Thr Trp Asp Ser Ser Leu Asn Gly
1               5

<210> SEQ ID NO 7
<211> LENGTH: 121
<212> TYPE: PRT
<213> ORGANISM: Artificial Sequence
<220> FEATURE:
<223> OTHER INFORMATION: Synthetic (a polypeptide capable of being used
      as a heavy chain variable region of an anti-VEGF-C antibody)

<400> SEQUENCE: 7

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Ala Ile Ser Tyr Asp Asn Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Pro Tyr Leu Ala Arg Leu Asn Thr Phe Asp Tyr Trp Gly
            100                 105                 110

Gln Gly Thr Leu Val Thr Val Ser Ser
        115                 120

<210> SEQ ID NO 8
<211> LENGTH: 108
<212> TYPE: PRT
<213> ORGANISM: Artificial Sequence
<220> FEATURE:
<223> OTHER INFORMATION: Synthetic (a polypeptide capable of being used
      as a light chain variable region of an anti-VEGF-C antibody)

<400> SEQUENCE: 8

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Asn Val Ser Trp Tyr Gln Gln Leu Pro Gly Thr Ala Pro Lys Leu Leu
        35                  40                  45

Ile Tyr Tyr Asn Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Ser Ser Leu
                85                  90                  95

Asn Gly Tyr Val Phe Gly Gly Gly Thr Lys Leu Thr
            100                 105

<210> SEQ ID NO 9
<211> LENGTH: 363
```

```
<212> TYPE: DNA
<213> ORGANISM: Artificial Sequence
<220> FEATURE:
<223> OTHER INFORMATION: Synthetic (polynucleotide encoding the
      polypeptide of SEQ ID NO: 7)

<400> SEQUENCE: 9
gaagtccagc tgctagaatc tgggggggc  ctggtccagc ctggtggatc tctcagatta    60
tcctgtgccg caagcggatt caccttctca tcttacgaca tgagttgggt gaggcaagcc   120
ccaggcaagg gcttggagtg ggtgagcgcg atctcctacg acaatggtag tacttactat   180
gccgattccg ttaaaggccg ctttacgatt agtagagata cagcaagaa  tacactgtat   240 ttgcagatga actccctgag agcagaggat actgctgtgt actattgcgc cagagacccc   300
tatctggctc ggctgaatac ctttgactac tggggacagg ggacacttgt gaccgtatca   360
agc                                                                  363

<210> SEQ ID NO 10
<211> LENGTH: 333
<212> TYPE: DNA
<213> ORGANISM: Artificial Sequence
<220> FEATURE:
<223> OTHER INFORMATION: Synthetic (polynucleotide encoding the
      polypeptide of SEQ ID NO: 8)

<400> SEQUENCE: 10
cagagtgtcc ttacccagcc cccatcagcc tccggtacgc ctggccagag agtgactata    60
agctgctctg gatcctcctc caatatcgga agcaacaacg tttcttggta ccagcaactg   120
cctggcacag cacctaagct gctcatttac tataattctc acagacccag cggggtgcca   180
gacagatttt ctggctcaaa gtcgggtacc tcagccagtc tggcaatcag cgggctgaga   240
tcagaggatg aagctgatta ttattgtgct acctgggaca gcagtctgaa tggctacgtg   300
ttcggcgggg gaacaaaatt gactgtccta ggc                                333
```